United States Patent [19]

Tobey

[11] Patent Number: 5,766,638

[45] Date of Patent: Jun. 16, 1998

[54] HYDROXYPROPYL METHOCELLULOSE ETHER COMPOSITIONS FOR REDUCTION OF SERUM LIPID LEVELS

[75] Inventor: Stephen W. Tobey, Midland, Mich.

[73] Assignee: The Dow Chemical Company, Midland, Mich.

[21] Appl. No.: 569,332

[22] Filed: Dec. 8, 1995

[51] Int. Cl.$^6$ .......................... A61K 9/50; A61K 31/715
[52] U.S. Cl. ........................ 424/499; 514/57; 514/824
[58] Field of Search .................. 424/499; 514/57, 514/824

[56] References Cited

U.S. PATENT DOCUMENTS

| | | | |
|---|---|---|---|
| 2,701,782 | 2/1955 | Culter | 167/56 |
| 3,308,020 | 3/1967 | Wolf et al. | 167/65 |
| 3,342,805 | 9/1967 | Callihan | 260/232 |
| 3,383,281 | 5/1968 | Wolf et al. | 167/65 |
| 3,388,082 | 6/1968 | Rodgers et al. | 260/17 |
| 3,499,960 | 3/1970 | Macek et al. | 424/33 |
| 3,709,876 | 1/1973 | Glomski et al. | 260/231 A |
| 3,947,272 | 3/1976 | Eynde et al. | 96/56.5 |
| 4,410,693 | 10/1983 | Gibson et al. | 536/56 |
| 4,477,657 | 10/1984 | Strange et al. | 536/91 |
| 4,626,287 | 12/1986 | Shah et al. | 106/197.1 |
| 4,671,823 | 6/1987 | Shah et al. | 106/197.1 |
| 4,696,762 | 9/1987 | Sander et al. | 252/311 |
| 4,732,917 | 3/1988 | Shah | 514/781 |
| 4,820,813 | 4/1989 | Schulz | 536/84 |
| 5,266,334 | 11/1993 | Phadke | 424/489 |
| 5,281,584 | 1/1994 | Tobey | 514/57 |
| 5,372,998 | 12/1994 | Kokubo et al. | 514/57 |

FOREIGN PATENT DOCUMENTS

| | | |
|---|---|---|
| 0119479 | 9/1984 | European Pat. Off. . |
| 0309029 | 3/1989 | European Pat. Off. . |
| 0323666 | 7/1989 | European Pat. Off. . |
| 0362926 | 4/1990 | European Pat. Off. . |
| 1280150 | 7/1972 | United Kingdom . |
| 1285776 | 8/1972 | United Kingdom . |
| 9201511 | 2/1992 | WIPO . |
| 9201515 | 2/1992 | WIPO . |

OTHER PUBLICATIONS

Ohata, Isao. "Studies on the Anti–Arteriosclerotic Drug . . . ", *Nichi Idaishi*, vol. 51 No. 3 pp. 20(302)–34(316), 1984.

*Primary Examiner*—Kimberly Jordan
*Attorney, Agent, or Firm*—Karen L. Kimble

[57] ABSTRACT

The present invention concerns cool-water dispersible powder formulations of high molecular weight hydroxypropyl methylcellulose which has been milled to a specified particle size, with or without encrustation or other surface treatment, for dispersion into consumable liquids or for formulation of dry-mix powders, sauces, instant set puddings and baked goods for human consumption. The formulation is used for reduction of serum cholesterol levels. A process for preparing the formulation and its mode of administration is also provided.

19 Claims, No Drawings

HYDROXYPROPYL METHOCELLULOSE ETHER COMPOSITIONS FOR REDUCTION OF SERUM LIPID LEVELS

BACKGROUND OF THE INVENTION

This invention relates to dry powder and dry mix formulations of water-soluble, high-viscosity grade hydroxypropyl methylcellulose compositions for non-systemic use in effecting reduction in serum lipid levels, particularly total serum cholesterol, and LDL cholesterol levels.

The use of cellulose ethers in edible compositions and, in particular, pharmaceutical products, is well known. A common function of the cellulose ether in such uses is to serve as a controlled release agent. Typically, however, only minimal quantities of the cellulose ether, representing only a small percentage of a total formulation, are required in such uses.

A variety of compounds are currently known to be useful in reducing serum cholesterol levels in humans. However, many of these compounds, including both systemic and non-systemic compounds, have undesirable side effects or have certain characteristics that lead to difficulties in patient compliance with their use. For example, characteristics such as the sandiness, grittiness, throat irritation, difficulty in dispersion and phase separation of known non-systemic compounds lead to very poor patient compliance. Accordingly, the search for new non-systemic compounds useful in reducing serum cholesterol levels in humans continues to be an important field of research.

Cholestyramine is an important, non-systemic compound known to be effective in treating high blood cholesterol levels (also known as hypercholesterolemia), which are believed to be responsible in many cases for arteriosclerosis in humans. Cholestyramine, which is typically orally consumed in order to effect its cholesterol lowering or controlling properties, is astringent and unpleasant to swallow. The cholestyramine also has the side effect of inducing constipation. Processes and compositions including cholestyramine are known, such as those described in U.S. Pat. No. 3,308,020, U.S. Pat No. 3,383,281, U.S. Pat. No. 3,499,960 and U.S. Pat. No. 3,947,272.

It is known that substantially water soluble vegetable fibers such as psyllium, guar, and β-glucans may exert cholesterol lowering effects, but these soluble fibers are not very efficacious on a per gram basis. Also, because these soluble vegetable fibers are easily metabolized by colonic bacteria (causing extensive anaerobic production of methane, carbon dioxide, and hydrogen), these vegetable fibers are known to cause gross flatulence, bloating and grave abdominal discomfort when administered to humans in therapeutically effective doses. Furthermore, psyllium seed husk is typically contaminated with fragments of proteinaceous hull, which carries the allergens known to be associated with psyllium.

Ground psyllium seed is recognized for its ability to lower serum cholesterol levels in human patients. EP-A-0 362 926 describes the use of products containing psyllium seed husk known to be effective in reducing human serum cholesterol levels. EP-A-0 309 029 describes cookies containing psyllium and polyol polyesters which are useful in reducing blood cholesterol levels.

EP-A-0 323 666 describes the use of products containing cholestyramine in combination with psyllium or with polyol polyesters as orally administered cholesterol-lowering compositions.

Recently, various forms and formulations of hydroxypropyl methylcellulose (HPMC) have been discussed as cholesterol lowering agents (e.g., WO-A-US92/01515, and WO-A-US92/01511). U.S. Pat. No. 5,281,584 discusses a baked formulation for similar use. Although these references use an HPMC of high number average molecular weight, the formulations are not those of the present invention.

Previously, cellulose ethers, such as carboxymethylcellulose and methylcellulose, have been administered as bulk laxatives in the form of tablets, powders (e.g., EP-B1-02 1992 479), and suspensions in highly concentrated sugar solutions. These cellulose ethers differ significantly (e.g., chemical structure, molecular weight, and viscosity) from the HPMC of the present invention and have a different intended use.

In order to administer non-systemic compounds, such as those discussed above, a suitable formulation is required. For various reasons, such formulations are not easily prepared for cellulose ethers.

Tableted cellulose ethers, for example, do not readily disperse and dissolve in the digestive tract. The outer portion of the tablet quickly forms a gel-like hydrated coating of the partially hydrated cellulose ether which inhibits break-up of the tablet and greatly retards hydration of the interior portions of the tablet. Accordingly, the tablet is often excreted as an intact gel-coated mass. Thus, when employed in tablet form, cellulose ethers have greatly reduced efficacy.

British Patent 1,280,150 teaches that blending of a cellulose ether with from 1 to 20 percent of a water-soluble food, such as sucrose, will aid dissolution of the cellulose ether in cold water, without formation of lumps. This was an attempt to improve upon earlier known formulations for cellulose ethers which had covalently bonded glyoxal. Glyoxal is not desired, as it is toxic when ingested.

A bulk laxative composition is described in EP-B-0 119 479 which teaches that 2 grams of finely powdered 100,000 cP viscosity grade hydroxypropyl methylcellulose dispersed in about 25 grams of Tang™ brand orange flavored instant drink mix (distributed by General Foods Corporation, White Plains, N.Y., USA), provides a formulated product for delivering a therapeutic dose of the cellulose ether to treat constipation.

Various cellulose ethers have been used as bulk laxatives wherein a concentrated sugar solution is first prepared in water and the cellulose ether is then dispersed therein. This method was used to minimize full hydration and dissolution of the cellulose ether, and to minimize viscosity buildup. (For example, see U.S. Pat. No. 2,701,782.) However, such suspensions are very thick and semi-gelatinous, have a slimy mouth feel, are extremely sweet, and are thus not appealing to the patient.

Depak Phadke et al., U.S. Pat. No. 5,266,334, discloses water-dispersible, sugar-free powder mixtures of maltodextrin with methylcellulose or HPMC in formulations for use as bulk laxatives. The cellulose ether is taught as being present as a fine powder in admixture, not as an encrusted material. The HPMC particle size is taught to be less than 40 mesh (400 μm), preferably less than 60 mesh (250 μm).

Dhirin Shah et al., U.S. Pat. No. 4,732,917, teaches the preparation of sucrose coated low molecular weight methylcellulose where the ratio of methylcellulose to sucrose is about 2:1, and the dry powder has the consistency of fine flour. This dry powder, prepared by the method described in the patent, cannot be dispersed directly into water without gelling and requires a "carrier" formulation.

Evidence of the unpalatability of non-systemic compositions currently being marketed to treat hypercholesterolemia is the well known low rate of compliance by human patients in adhering to diets requiring daily consumption of these compositions. This low compliance indicates a definite need for hypocholesteremia-controlling compositions which are more palatable and more effective than known compositions.

The present invention addresses the noncompliance problem by using a composition in a method for reducing serum cholesterol levels in human patients by providing a suitable formulation to aid in the efficacy of the HPMC and promote compliance by the patient.

SUMMARY OF THE INVENTION

The present invention concerns cool-water dispersible, dry powder compositions for non-systemic use of high molecular weight (HMW) HPMC which has been milled to a specified particle size distribution, with or without encrustation or other surface treatment, for dispersion into consumable liquids or for consumption in reconstituted dry mixes, sauces, instant-set puddings and baked goods. The compositions are used for reduction of serum cholesterol levels in mammals, especially humans. Processes for preparing the formulations and their modes of administration are also provided.

A cool-water dispersible, dry mix powder hydroxypropyl methylcellulose composition of the present invention comprises an hydroxypropyl methylcellulose which has (a) a particle size distribution having an upper limit of less than or equal to five percent of the particles of hydroxypropyl methylcellulose larger than about 600 μm and having a lower limit of less than or equal to fifty percent of the particles of hydroxypropyl methylcellulose smaller than about 180 μm; and (b) a viscosity, in a 2 weight percent aqueous solution at 20° C., from greater than about 10,000 cP to 2,000,000 cP.

A preferred embodiment of the present invention comprises encrusting the above hydroxypropyl methylcellulose with an encrusting agent such as sucrose, maltodextrin or other suitable encrusting agent.

The present compositions of the present invention can be used for reducing serum cholesterol in a non-ruminant mammal, especially humans, in need of such treatment which comprises administering to the mammal from about 1 to about 8 g per dose of the above hydroxypropyl methylcellulose composition, with or without encrustation.

A process for preparing an aqueous dispersion of a water soluble high molecular weight hydroxypropyl methylcellulose requires only mild agitation in cool water which comprises:

a) grinding, milling or screening a high molecular weight hydroxypropyl methylcellulose to obtain a particle size distribution with less than 50% of the particles smaller than about 180 μm and less than 5% of the particles larger than about 600 μm; and b) optionally encrusting the high molecular weight hydroxypropyl methylcellulose with an encrusting agent of a natural sugar or maltodextrin at a ratio of the encrusting agent relative to the hydroxypropyl methylcellulose from about 0.5:1 to about 2:1 w/w, and then milling or screening the encrusted hydroxypropyl methylcellulose through a 16 mesh screen; and c) optionally adding a flavoring agent; and d) optionally adding one or more additive materials selected from the group consisting of preservatives, buffers, colorants, anti-caking agents, antioxidants, opacifiers, vitamins, minerals, and setting agents.

DETAILED DESCRIPTION OF THE INVENTION

The formulations of the present invention provide high molecular weight (HMW) HPMC in a highly-hydrated, predispersed form without resorting to hot-water dispersion (i.e., above the thermal gelation temperature of the HPMC). In the compositions of the present invention, the HPMC is present in a daily consumption amount by humans of from about 2 grams to about 30 grams.

For the purposes of this invention several of the terms used herein are defined as follows.

"HPMC" means hydroxypropyl methylcellulose having a number average molecular weight greater than about 80,000 daltons (10,000 cP viscosity grade).

"High molecular weight" for the HPMC ethers of this invention refers to those HPMC ethers having a number-average molecular weight greater than about 80,000 daltons. HPMC ethers having a number average molecular weight greater than 150,000 daltons are designated as having ultra-high molecular weight (UHMW). HPMC for use in this invention has a number average molecular weight preferably greater than about 100,000 daltons, more preferably greater than about 140,000 daltons, and most preferably greater than about 150,000 daltons. The HPMC ethers have an upper limit for number average molecular weight of less than or equal to 400,000 daltons. HPMC of the type used in this invention has a methoxy substitution of from about 19 percent to about 24 percent and a hydroxypropoxy substitution of from about 4 percent to about 12 percent.

In order to correlate the number average molecular weight to viscosity grade, the following table is provided.

CORRELATION TABLE

| Number Average Molecular Weight $M_n$, daltons | Viscosity Grade cP |
| --- | --- |
| 80,000 | 10,000 |
| 100,000 | 25,000 |
| 140,000 | 50,000 |
| 150,000 | 100,000 |
| 220,000 | 400,000 |
| 260,000 | 500,000 |
| 400,000 | 2,000,000 |

The HPMCs of this invention are those which are of a high-viscosity grade or are of high viscosity. By "high-viscosity grade" or "high viscosity" is meant those cellulose ethers which, when in a 2 weight percent aqueous solution, exhibit a viscosity at 20° C. of greater than about 10,000 centipoise (cP) (10,000 mPa.s) and may have a viscosity as high as 2,000,000 cP (2,000,000 mPa.s). Such viscosities may generally be measured by conventional methods, for example, by measuring the viscosity of an aqueous solution of the polymers at the desired concentration in Ubbelohde capillary viscometer tubes at the specified temperature. The cellulose ethers of this invention, when in a 2 weight percent aqueous solution at 20° C., exhibit a viscosity ranging from about 10,000 cP (10,000 mPa.s), preferably from about 25,000 cP (25,000 mPa.s), to about 2,000,000 cP (2,000,000 mPa.s). More preferably, the cellulose ethers of this invention, when in a 2 weight percent aqueous solution at 20° C., exhibit a viscosity ranging from about 50,000 cP to about 800,000 cP, most preferably from about 100,000 cP (100,000 mPa.s) to about 500,000 cP (500,000 mPa.s). Conversely, by "low-viscosity grade" is meant those cellulose ethers which, when in a 2 weight percent aqueous solution, exhibit a viscosity at 20° C. below about 10,000 cP (10,000 mPa.s).

For the purposes of this invention, milling and screening of the HPMC compositions can be carried out on any equipment which is capable of achieving the specified particle size distribution without subjecting the composition to heating above 50° C. For the preparation of HPMC fluff, an Alpine brand fan beater mill fit with a screen having 0.4 mm diameter holes gave satisfactory results. A variety of other mild intensity mechanical impact mills are capable of giving similar results, including wing beater, pin, hammer and knife mills. For preparation of the granulated derivatives, grinding the dried encrusted HPMC through a fitz brand mill with the appropriate screen size provides the desired particle size distribution.

When the HPMC of this invention is milled and/or screened until it has the desired particle size distribution, the HPMC thus formed is termed the pharmaceutically active ingredient. This pharmaceutically active ingredient is a white fluffy solid of a particular particle size distribution, and is referred to herein as "fluff" or the "pharmaceutically active ingredient". When the fluff is modified with an encrusting agent so that the composition of the HPMC has an encrusting component, and a particular particle size distribution is achieved by milling and/or sieving, it is referred to as a "granulated derivative". When either the fluff or the granulated derivative is blended with other ingredients to obtain the final dosage form, it is referred to herein as a "formulated product". When all or any of the forms (i.e., fluff, granulated derivative and formulated product) are intended, they are referred to herein as "compositions".

For the compositions to exhibit palatability in the formulated product (especially in drinkable formulated products), the particle size distribution of the HPMC fluff is important. The upper limit on the desired fluff particle size distribution is that it have less than or equal to five percent ($\leq 5\%$) of the HPMC particles larger than about 600 µm (0.6 mm, 30 mesh screen), and preferably less than about 2%. Larger particles cause grittiness in the liquid form of the formulated product. The lower limit on the fluff particle size distribution is that it have less than or equal to fifty percent ($\leq 50\%$) of the HPMC particles smaller than about 180 µm (0.18 mm, 80 mesh screen), preferably less than about forty percent (40%), and more preferably less than about thirty percent (30%). Small particles cause the formation of froth, air pockets, slubs, and rapid viscosity buildup when the formulated product is dispersed into water or other liquid for consumption. The above mesh sizes are US sieve series sizes, ASTM E-11-61.

When conventional finely powdered UHMW HPMC (100,000 cP viscosity grade, 80% through 80 mesh screen) is incorporated into a baked product (e.g., a 25–30 g cookie containing 5 g HPMC), the cookie literally turns into chewing gum when chewed. This result is unacceptable in a formulated product for the purposes of the present invention. However, when this same HPMC is milled through a 0.4 mm screen on an Alpine mill, fluff is obtained. This fluff has a much lower surface area than the conventional powder. When this fluff is incorporated into a cookie (eg., a 25–30 g cookie containing 5 g of HPMC fluff), the cookie can be chewed and swallowed with essentially no gumminess. Thus palatability is greatly enhanced.

When conventional finely powdered HPMC (100,000 cP viscosity grade; 80% through 80 mesh screen; 2.5 to 5 g) is dry dispersed in 28 g of a powdered orange flavored drink mix, the resulting formulation when mixed into 250 mL of cool water (0°–20° C.), barely disperses at the 2.5 g level and clumps severely at the 5 g level. In contrast, when HPMC fluff of the same viscosity grade (2.5 to 5 g) is dry dispersed in 28 g of a powdered orange flavored drink mix, the formulated product disperses readily at both concentrations when mixed into 250 mL of cool water.

The compositions of the present invention provide HPMC in a form that is readily dispersible in cool water (0°–20° C.) and suitable for preparation of palatable oral dosages containing from about 1 to about 8 g, preferably from about 2 to 5 g HPMC, per dose for oral administration in the treatment of elevated serum cholesterol levels. The large quantity of HPMC that may be dispersed in water is very surprising and is far in excess of what was previously believed possible while still maintaining a palatable formulation.

The fluff form of HPMC has the advantage of being able to deliver the HPMC in a highly hydrated and predispersed form into the stomach, without resorting to either comestible dosage forms or to hot water/hot liquid dispersion of the HPMC. In this context, "comestible" implies incorporation of the HPMC into a baked cookie or biscuit form, normally comprising about 5 g of the HPMC in a baked good of about 25 to 35 g total weight. The comestible is to be chewed and accompanied by ingestion of about 8 ounces (225 g) of water or other liquid. In this same context, "hot water" or "hot liquid" dispersion is taken to be dispersion into water or other liquid (for example, lemonade) at a temperature of about 85° C. or higher. This temperature is well above the known (50°–70° C.) thermal gelation temperature range of the present HPMC.

The fluff form of HPMC permits administering HPMC in doses from about 1 g per dose, especially from greater than 3 g per dose, and more especially for doses equal to or greater than 5 g per dose, in a palatable manner. These doses of HPMC were previously very difficult to attain while retaining sufficient palatability to encourage patient compliance. It was very unexpected that although HPMC fluff has a large particle size, it is not gritty when dispersed in aqueous fluids.

The fact that the fluff form permits HPMC to be prehydrated for oral administration, while the formulation containing the dry fluff can be both fat and cholesterol free, is a very important consideration in any non-systemic cholesterol treatment formulation. Thus the present compositions and formulated products have significant advantages over those previously known.

Optionally, the HPMC fluff can be coated with an encrusting component to make a granulated derivative. The encrusting agent can be a natural sugar, such as sucrose, glucose, fructose, corn syrup solids, and the like, where sucrose is preferred. The amount of encrusting component, when a natural sugar, relative to the HPMC is from about 0.25:1 to about 4:1 (w/w), preferably from about 0.5:1 to about 3:1 (w/w), more preferably from about 0.75:1 to about 2:1 (w/w), most preferably about 1:1 (w/w).

The encrusting agent can also be selected from low molecular weight sugar polymers and sugar derivatives and their mixtures, such as maltodextrins, sorbitol and the like. The preferred ratio of HPMC fluff to encrusting component remains about 1:1 (w/w). Surprisingly, the resulting granulate can be milled to a large particle size distribution and retain excellent properties. Handling the dry powder is very easy and little unencrusted HPMC is found after the milling. When a granulated derivative (1:1 w/w) UHMW HPMC- :sucrose was made, and ground through a 16 mesh screen so that more than 40% of the particles fell between 18 mesh and 25 mesh, another 30% between 25 and 40 mesh and only about 10% passed through a 60 mesh, the granulated derivative displayed remarkable properties. This granulated derivative (e.g., 5 to 10 g) can be dispersed directly into 6–8 oz of cool fruit juices or water, without resorting to any further formulation aids, to provide smooth, grit-free dispersions with very slow viscosity build.

The granulated derivative HPMC can be readily admixed with other dry mix powders to create a formulated product. For example, usually a flavoring agent is present in the formulated product. Examples of added flavorings are powdered fruit drinks, powdered hot drink mixes such as cocoa mix, powdered lemonade mix and the like. Such dry mix powders are well known to persons skilled in this art and have been discussed as well in the various references given hereinabove.

In addition to the foregoing, one or more other additive materials such as preservatives, buffers, colorants, anti-caking agents, antioxidants, opacifiers, vitamins and minerals, and setting agents, which are commonly employed in food, beverage or drug substances may be employed in a conventional manner.

The high-viscosity grade, water-soluble cellulose ethers of the present invention are inert, non-ionic cellulose ethers which are known to be edible. The high-viscosity grade cellulose ethers used in an edible composition are characterized in that the high-viscosity grade cellulose ethers meet the specifications of the United States Pharmacopeia (USP) and: (1) are resistant to bacterial fermentation in the large bowel of the non-ruminant mammals and, therefore, do not cause gas production resulting from such fermentation, (2) are substantially inert to attack by enzymes found in the digestive tract, (3) do not produce the allergic responses characteristic of certain vegetable fibers, and (4) interfere minimally with micronutrient absorption.

The present UHMW HPMC thus differs from the cellulose ethers mentioned in the above references, such as the bulk laxative composition described in EP-B-0 119 479, because of the quantity of the HPMC per dose, the high molecular weight and viscosity of the particular HPMC of the present invention, and the particle size distribution of the HPMC employed.

The cellulose ethers used in the present invention may be prepared by any of a number of known processes. Illustrative processes are set forth in U.S. Pat. No. 3,342,805; U.S. Pat. No. 3,388,082; U.S. Pat. No. 3,709,876; U.S. Pat. No. 4,477,657; U.S. Pat. No. 4,410,693; and U.S. Pat. No. 4,820,813, the disclosures of which are hereby incorporated by reference. Generally, a specific cellulose ether is prepared by the formation of an alkali cellulose by the addition of sodium hydroxide to cellulose. The alkali cellulose is then reacted with an appropriate alkylating agent or agents. Thereafter, the cellulose ether product is purified, dried, and ground. U.S. Pat. No. 4,820,813 teaches the preparation of a high molecular weight cellulose ether which is ground under conditions of mild mechanical impact such as those encountered in a high speed, air swept impact mill (e.g., an Alpine mill). This mild impact process is a cutting or dicing process for particle size reduction, which preserves molecular weight and, therefore, viscosity. The method of measuring viscosity affects the resulting value obtained since solutions of high molecular weight cellulose ethers are shear thinning. Thus viscosity values are method dependent. For example, when the viscosity of a solution of one HPMC was measured using a rotational viscometer at very slow speed, the viscosity reading was 106,000 cP (0.5 rpm, 1 sec$^{-1}$ shear); but when the viscosity was determined according to the USP method in which the viscosity of a 1% solution is measured using a Ubbelohde capillary viscometer and extrapolated to a concentration of 2%, the viscosity value was 420,000 cP.

From other experiments, it is known that HPMC ground in an Alpine mill using a 2.0 mm bore screen provides aqueous dispersions that exhibit a taste and/or feel of being gritty. Thus an inappropriate particle size makes such incorrectly ground HPMCs unsuitable for the present invention.

Generally, 2.0 mm bore screen Alpine milled HPMC does not produce a suitable pharmaceutically active ingredient or fluff. The reason is that the particle size distribution of this product contains numerous fluff particles ($\geq 5\%$) larger in size than 600 µm (30 mesh), and these fluff particles impart grittiness to liquid suspensions made from a formulated product containing this fluff. Thus the product has poor palatability. The fluff particles are also too large to permit an homogeneous character to the formulated product dry powder mix, because the fluff particles tend to segregate out of the dry powder mix.

Similarly, an HPMC ($\geq 10,000$ cP viscosity grade) milled to a fine powder as generally known in the art is unsatisfactory as a pharmaceutically active ingredient for the purposes of this invention. Such conventionally ball milled HPMC particles have an average particle size of less than 180 µm (80 mesh). Such powders carry adhering air into the liquid suspensions prepared from them, which causes frothing and foaming. The HPMC powder particles tend to reaggregate and form dry-centered lumps due to their poor wet-out properties (anthropomorphic), while causing rapid viscosity buildup from the few particles which do hydrate in suspension, due to their very high surface area and rapid dissolution. This rapid (<3 min) viscosity buildup quickly renders the suspension gelatinous and unfit or unpalatable for consumption.

The cellulose ethers employed in the present invention must be readily water-soluble. As used herein, the term "readily water-soluble" means that two grams of a powdered or ground cellulose ether of the present invention can be dispersed by stirring into 100 grams of water at a temperature between about 0° C. and 100° C. to provide, upon complete hydration, a substantially clear solution or dispersion (gel) when the dispersion is brought to a temperature of 20° C.

A unique characteristic of the formulated products of the present invention is that they can all be dispersed directly into cool liquids, at temperatures below the thermal gelation range of HPMC (50°–70° C.). Another unique attribute of the formulated products of this invention is that they can be directly dispersed into cool water or other aqueous based systems to obtain palatable products for human consumption, using only simple spoon stirring. With the particle size distribution of the fluff and/or granulated derivative as specified herein, it is not necessary to resort to either the use of hot liquids or high shear stirring devices to obtain palatable, non-gooey, non-gelatinous dispersions of the HPMC pharmaceutically active ingredient.

For comparison, one attempted method of administering 2–3 g of UHMW HPMC to human subjects was to admix HPMC fluff with about 15 g of sugar-free hot chocolate drink mix, then stir this formulated product into 250 mL of hot (80° C.) water to form a hot beverage. In practice, the beverage preparation proceeds smoothly. The water temperature is well above the 50°–70° C. thermal gelation temperature of the HPMC, so the HPMC simply disperses in the hot liquid without appreciably hydrating or dissolving. However, as the beverage cools, hydration and dissolution of the HPMC begins. By the time the beverage has cooled to the upper limit of human thermal endurance (i.e., about 50° C.), the HPMC has gelatinized in the beverage to a single, slithery mucousal mass which is absolutely nauseating.

Formulated products containing the HPMCs of this invention can be prepared by mild agitation of mixtures of the fluff or granulated derivative with the other dry powder formulating agents, using any suitable dry powder blending equipment (e.g., ribbon, double cone, Lodige or the like) or by stirring or shaking using the usual appliances in a kitchen, or by manual means.

No fats or oils are added to (unless desired for a flavoring or such purpose) or are required in the present formulated products.

By using the coarser HPMC fluff, such as is obtained by milling through a 0.4 mm screen in an Alpine mill, a slower dissolution rate of the HPMC is achieved than with the conventional, fine powder form of Methocel™ (a trademark of The Dow Chemical Company) cellulose ether. As described above, even without the use of an encrusting agent, e.g., sucrose or maltodextrin, a suitable dispersion can be achieved.

The following scheme illustrates processes for preparing the compositions of the present invention.

PROCESS SCHEME

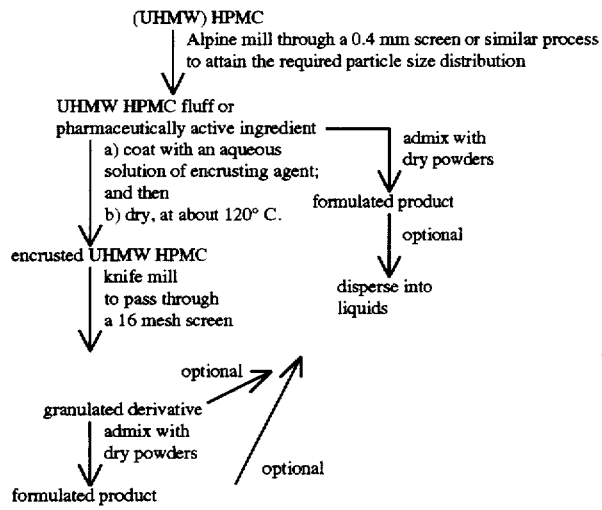

The compositions of the present invention, particularly the granulated derivative described in Example 3 containing UHMW HPMC, provide exceptional ease of dispersion into water and aqueous liquids and excellent organoleptic properties therein, while minimizing the stir time necessary to achieve satisfactory dispersion and hydration. Further, the present compositions prolong the time before excessive viscosity build occurs. This is especially important when larger doses (e.g., 5.0 g) of the UHMW HPMC are desired or required for treatment.

The compositions of this invention are readily dispersible into a variety of aqueous liquids, such as fruit juices, aqueous nectars and extracts (such as apple, orange and apricot). The compositions also mix well with other formulated dry-mix powders (such as Tang™ brand orange drink mix, SlimFast™ and Horlicks) that are intended to be reconstituted with water or milk. The compositions are also readily dispersible into applesauce, instant set dry pudding mixes and tapioca, baked good dry mixes (such as cookies and muffins), granola bar compositions, and the like.

The Schultz patent (U.S. Pat. No. 4,820,813, the disclosure of which is hereby incorporated by reference) discloses one method of making finely powdered UHMW HPMC which involves low impact grinding of UHMW HPMC. Although this method could be used to produce the present fluff, he did not do so. The particle size distribution of the HPMC made was below 80 mesh. The purpose of his efforts was to obtain a very fine particle size to mimic the known methylcullose products while maintaining high viscosity.

The compositions of the present invention having the UHMW HPMC present, may be used to reduce serum cholesterol. To achieve this result, the active ingredient (UHMW HPMC) should be present at a level of about 1 to 8 g per dose, preferably from about 2.5 to about 5 g per dose, in the formulated product. The total number of doses administered per day will depend on the level of reduction desired for the particular patient. Typically, about 2 to 3 doses containing about 1 to 8 g each are administered. Thus from about 2 to about 25 g per day is administered in divided doses.

While not wishing to be bound by theory, it is believed that the advantageous properties of the HPMC compositions of the present invention and results obtained from their use are due to their particular particle size distribution and greater molecular weight, especially for the UHMW HPMC, i.e. its molecular weight, viscosity grade and dispersibility. Any procedure which enables these requirements of particle size distribution and molecular weight for the HPMC to be attained is within the scope of the present invention.

The invention will be further clarified by a consideration of the following examples, which are intended to be purely exemplary of the present invention.

EXAMPLE 1

UHMW HPMC fluff, 2.5 gram (g), milled through a 0.4 millimeter (mm) bore screen on an Alpine mill, was mixed in a 10 ounce (oz) plastic cup with 2 level tablespoons (30.8 g) of Tang™ brand dry powder orange drink mix. The admixture was accomplished simply by stirring with a spoon. A homogeneous particulate/particulate dispersion in the form of a orange colored, dry powder mix was obtained.

To this dry powder mixture was added 8 oz (224 g) of cool (about 15° C.) tap water all at once, and the suspension was spoon stirred for about 1 minute. At the end of the stirring, a cool, smooth, palatable, pulpy textured orange drink composition was obtained.

With occasional stirring to test the viscosity of the dispersion formed, the orange drink was consumed in portions over the subsequent 6 minutes at about 30 second intervals. The orange drink continued to be tasty, totally palatable and free of objectionable slubs, dry-centered lumps or any other objectionable particulate matter.

A composition having 2.5 g of UHMW HPMC in a liquid formulation form was thus achieved without heating the liquid above the thermal gel point of the UHMW HPMC.

EXAMPLE 2

UHMW HPMC fluff, 5.1 g, milled as described in Example 1, was mixed in a 10 oz plastic cup with 2 level tablespoons (28.6 g) of Tang™ brand dry powder orange drink mix. The admixture was easily accomplished by stirring with a spoon. An homogeneous particulate/particulate dispersion in the form of a orange colored, dry powder mix was obtained.

To this dry powder mixture was added 225 g of cool (about 13° C.) tap water all at once, with spoon stirring. After 30 seconds of continued stirring, an homogeneous suspension with the texture of apricot nectar was obtained. This suspension was thoroughly palatable and free of dry particles.

With continued stirring, after about 60 seconds from the time of water addition, a thoroughly palatable orange drink mix was still extant. By 90 seconds, the suspension was thickening. At 120 seconds, thickening was further advanced. At 180 seconds, a soft, spoonable, jam-textured gel had begun to form. At 210 seconds, a soft gel was obtained which had the consistency of applesauce. If a formulation to be consumed at this later stage is desired, the orange flavoring is replaced by apple flavoring.

A composition having 5.1 g of UHMW HPMC in a fully suspended liquid form was thus achieved without recourse to heating the liquid above the thermal gel point of the HPMC.

EXAMPLE 3

A sucrose encrusted UHMW HPMC (1:1 w/w sucrose:UHMW HPMC) granulated derivative was prepared by wet-granulating one part by weight UHMW HPMC fluff with a hot (above 50° C.) aqueous solution of one part by weight sucrose in one part by weight of water. A moist, crumbly mass was obtained. The material was dried to a constant weight at about 120° C. The resulting dry granule was then milled and screened so that about 95% or more passed a 1.0 mm (US Standard No. 18) screen. The dry granulated derivative contains less than 1% w/w residual moisture. The assay of UHMW HPMC fluff present in the dry granulate is 50% by weight. The settled bulk density of the dry granulate is about 0.43 g/cc. The dry granulated derivative is a visually attractive, free-flowing, low dust granule that gives the dry granulated derivative excellent powder-flow and powder-spooning properties. This 1:1 sucrose encrusted granulated derivative of UHMW HPMC fluff was used in about 5 to 10 g quantities to make a variety of doses of various formulated products.

For example, the dry granulated derivative was readily dispersible directly into a variety of liquid juices and beverages, such as fruit juices, aqueous nectars and extracts (such as apple, orange and apricot). It dispersed smoothly into applesauce, mixed well with formulated dry-mix powders (such as Tang™ brand orange drink mix, SlimFast™ and Horlicks that are intended to be reconstituted with water or milk), and was readily usable by direct addition to a wide variety of baked good recipes, instant set dry pudding mixes, baked good dry mixes (such as cookies and muffins) and granola bar compositions.

EXAMPLE 4

The encrusting procedure of Example 3 was repeated using maltodextrin in place of sucrose as the encrusting component. A sugar-free granulated derivative was obtained which was suitable for use either as is as a formulated product, or in admixture with additional dry powder ingredients to form other formulated products.

EXAMPLE 5

Sample A:

UHMW HPMC (400,000 cP viscosity grade), 2.53 g, which had been milled through a 2.0 mm screen, was mixed with 30.8 g of Tang™ brand orange drink mix. This formulated product, 15.5 g, was placed in a 9 oz plastic cup and mixed with a plastic spoon. Mixing was difficult and incomplete in attempting to obtain a uniform dry mix. The fibrous UHMW HPMC tended to cling together in aggregates resembling white lichens. To the dry mix was added all at once 8 oz of cool water with spoon stirring. Many bubbles formed in the matrix and on top of the liquid as a froth. Stirring was continued for 1 minute. Many slubs appeared on the side of the cup and spoon. The mouth feel of about 2 tbsp of the mixture was gritty and grainy, and particles of moistened but incompletely hydrated UHMW HPMC were obvious.

Sample B:

UHMW HPMC (400,000 cP viscosity grade), 2.50 g, which had been milled as described in Example 1, was mixed with 25.2 g of Tang™ brand dry powder orange drink mix, placed in a 9 oz plastic cup, and mixed with a plastic spoon. Admixture of the powders was easy using the spoon. The aggregates of UHMW HPMC disentangle on spoon mixing and disperse into the Tang™ brand orange drink mix. To the resulting homogeneous looking formulated product was added all at once 8 oz of cool water (about 10° C.), and the mixture was stirred with a spoon. After 1 minute of mixing, the liquid showed some froth and only a few slubs as wet dots on the side of the glass, but no graininess in the mouth. Viscosity buildup was slow, with pulp-like particles of the UHMW HPMC suspended in the main body of the drink. The mixture was still totally acceptable for at least 5 more minutes before viscosity buildup was advanced.

Sample C:

Conventional, finely powdered HPMC (80,000 cP viscosity grade, ≧80% less than 80 mesh), 2.5 g, was spoon mixed with 25.2 g of Tang™ brand dry powder orange drink mix in a 9 oz plastic cup. To the resulting homogeneous looking powder mix (formulated product) was added all at once 8 oz of cool water (about 10° C.), and the mixture was stirred with a spoon. After 1 minute of mixing, the liquid showed much froth, with many bubbles in suspension. Taste testing revealed no graininess in the mouth at one minute, but the viscosity was building up very quickly. In less than 3 minutes the mixture was too viscous and too tacky to drink.

Sample D:

Sucrose encrusted (1:1 w/w) UHMW HPMC fluff (420,000 cP viscosity grade), 5.2 g, which had been course milled through a 16 mesh screen, was mixed with 25.2 g of Tang™ brand dry powder orange drink mix in a 9 oz plastic cup. The two powders were admixed easily with a plastic spoon. The resulting powder mix appeared heterogeneous with some large white particles obvious against the orange background. To this formulated product was added all at once 8 oz of cool water (about 10° C.), and the mixture was stirred with a spoon. No froth and no slubs formed. The liquid suspension looked like Tang™ with suspended pulp. At 1 minute, the mouth feel was characteristic of pulp in Tang™. After 3 minutes total time, the suspension showed very slow viscosity buildup, with no tackiness. After 5 minutes the suspension was still not viscous, and the suspended pulp-like particles were very soft. At 7 minutes there was no appreciable difference in mouth feel. At 12 minutes, the pulp-like particles were gloppy and viscosity was building.

Sample E:

Sucrose encrusted (1:1 w/w) UHMW HPMC fluff (420,000 cP viscosity grade, milled as described in Example 1), 5.1 g. which had been coarse milled through a 16 mm screen. was placed in a 9 oz plastic cup. with no additional formulation components. To the neat powder was added all at once 8 oz of cool water (about 10° C.). and the mixture was stirred with a spoon. No froth or slubs formed. At 1 minute, the suspension consisted of clear gel particles in water. There were no foam and no opaque gel particles (fish eyes) present. This stable, easily flowable aqueous dispersion persisted for at least 10 minutes. By 13 minutes, the dispersion had the consistency of mucous. At 25 minutes, a soft runny gel had formed.

Sample F:

When Sample E was carried out by pouring 5.0 g of the encrusted UHMW HPMC granulated derivative into the water, similar results to Sample E were obtained.

This shows the versatility of 1:1 Sucrose encrusted UHMW HPMC granulated derivative as a formulated product.

EXAMPLE 6

When the encrusted UHMW HPMC granulated derivative of Example 5, Samples E and F, was used, this composition was found to be very suitable both for further incorporation into final formulated products, and as a final formulated product in its own right. It is important that the granulated derivative or formulated product can be dispersed into either cool water (0°–20° C.), or warm water or heated beverages (40°–50° C.), with simple spoon stirring. Under these conditions viscosity buildup was slow, and grittiness was avoided. The granules of this granulated derivative are large. The particle size distribution of the granulated derivative was in the range of about 75% larger than 40 mesh (420 µm) but smaller than 16 mesh (1200 µm), and less than about 10% smaller than 80 mesh (180 µm). Yet, when this encrusted UHMW HPMC derivative was dispersed in water it rapidly formed individual gels which had a mouth feel characteristic of soft pulp particles. Suspensions of these gels retain acceptable viscosity for at least 4 minutes (2.5 g UHMW HPMC equivalent; 8 oz dispersing liquid).

EXAMPLE 7

Sucrose encrusted (1:1 w/w) UHMW HPMC (420,000 cP viscosity grade, as described in Example 6), 5.9 g, was stirred into a 4 oz cold (10° C.) applesauce all at once. A totally palatable applesauce suspension of the granulated derivative was obtained. The viscosity, taste, and texture of the applesauce suspension remained stable and appealing for at least 15 minutes.

EXAMPLE 8

UHMW HPMC fluff (420,000 cP viscosity grade, milled as described in Example 1), 5.0 g. was admixed with 10.0 g JELL-O™ brand sugar-free instant chocolate fudge dry powder pudding mix in a 10 oz cup. This resulting formulated product was an homogeneous dry brown powder mix. To this powder mix was added all at once 6 oz (178 g) cold (12° C.) 2% butterfat milk. The mixture was spoon stirred for 2 minutes. A thick, smooth pudding resulted which exhibited excellent mouth feel and flavor.

Other embodiments of the invention will be apparent to those skilled in the art from a consideration of this specification or practice of the invention disclosed herein. It is intended that the specification and examples be considered as exemplary only, with the true scope and spirit of the invention being indicated by the following claims.

What is claimed is:

1. A cool-water dispersible, dry mix powder hydroxypropyl methylcellulose composition wherein an encrusting component is present which coats the hydroxypropyl methylcellulose and the hydroxypropyl methylcellulose has (a) a particle size distribution having an upper limit of less than or equal to five percent of the particles of hydroxypropyl methylcellulose larger than about 600 µm and having a lower limit of less than or equal to fifty percent of the particles of hydroxypropyl methylcellulose smaller than about 180 µm; and (b) a viscosity, in a 2 weight percent aqueous solution at 20° C., from greater than about 10,000 to 20,000 cP.

2. The composition of claim 1 wherein the viscosity of the hydroxypropyl methylcellulose is from greater than about 25,000 to about 2,000,000 cP.

3. The composition of claim 1 wherein the viscosity of the hydroxypropyl methylcellulose is from greater than about 50,000 to about 800,000 cP.

4. The composition of claim 1 wherein the viscosity of the hydroxypropyl methylcellulose is from greater than about 200,000 to about 500,000 cP.

5. The composition of claim 1 further comprising a flavoring agent.

6. The composition of claim 1 further comprising one or more additive materials selected from the group consisting of preservatives, buffers, colorants, anti-caking agents, antioxidants, opacifiers, vitamins, minerals, and setting agents.

7. The composition of claim 1 wherein the ratio of the encrusting component relative to the hydroxypropyl methylcellulose is from about 0.5:1 to about 2:1 w/w.

8. The composition of claim 1 further comprising one or more additive materials selected from the group consisting of preservatives, buffers, colorants, anti-caking agents, antioxidants, opacifiers, vitamins and minerals, and setting agents.

9. A method of reducing serum cholesterol in a non-ruminant mammal in need thereof which comprises administering to the mammal from about 1 to about 8 g per dose of the composition of claim 1.

10. A method of reducing serum cholesterol in a non-ruminant mammal in need thereof which comprises administering to the mammal from about 1 to about 8 g per dose of the composition of claim 1.

11. The composition of claim 1 further comprising a flavoring agent.

12. A method of reducing serum cholesterol in a non-ruminant mammal in need thereof which comprises administering to the mammal from about 1 to about 8 g per dose of the composition of claim 11.

13. The composition of claim 1 wherein the encrusting component is a natural sugar.

14. The composition of claim 13 wherein the encrusting component is maltodextrin.

15. The composition of claim 13 wherein the natural sugar is sucrose.

16. The composition of claim 15 wherein the ratio of sucrose relative to the hydroxypropyl methylcellulose is from about 0.25:5 to about 4:1 w/w.

17. The composition of claim 15 wherein the ratio of sucrose relative to the hydroxypropyl methylcellulose is about 0.5:1 to about 3:1 w/w.

18. The composition of claim 15 wherein the ratio of sucrose relative to the hydroxypropyl methylcellulose is from about 0.75:1 to about 2:1 w/w.

19. The composition of claim 15 wherein the ratio of sucrose relative to the hydroxypropyl methylcellulose is about 1:1 w/w.

* * * * *